United States Patent [19]

Kato et al.

[11] 4,169,144

[45] Sep. 25, 1979

[54] TRIMETHOXYPHENYL ESTERS OF HOMOPIPERAZINE-N-MONOALKANOL AS VASODILATORS

[75] Inventors: Hideo Kato; Takaaki Mouri; Tomoyasu Nishikawa, all of Fukui, Japan

[73] Assignee: Hokuriku Pharmaceutical Co., Ltd., Fukui, Japan

[21] Appl. No.: 808,437

[22] Filed: Jun. 20, 1977

Related U.S. Application Data

[62] Division of Ser. No. 704,814, Jul. 13, 1976, Pat. No. 4,068,069, which is a division of Ser. No. 430,925, Jan. 24, 1976, Pat. No. 3,980,643.

[51] Int. Cl.$^2$ ............... A61K 31/55; C07D 243/08
[52] U.S. Cl. ..................... 424/244; 260/239.13 C
[58] Field of Search ............... 260/239 BC; 424/244

[56] References Cited

U.S. PATENT DOCUMENTS

3,532,685  10/1970  Arnold et al. ............... 260/239 BC

*Primary Examiner*—Donald G. Daus
*Assistant Examiner*—D. B. Springer
*Attorney, Agent, or Firm*—Burgess, Ryan and Wayne

[57] ABSTRACT

There is provided piperazine or homopiperazine-monoalkanol esters and salts thereof. These compounds are prepared by esterification of the corresponding alkanol compounds.

The novel compounds are characterized by therapeutic activity and specifically, analgetic, coronary vasodilative, anti-convulsant, and blood pressure-decreasing properties.

3 Claims, No Drawings

TRIMETHOXYPHENYL ESTERS OF HOMOPIPERAZINE-N-MONOALKANOL AS VASODILATORS

This application is a division of co-pending application Ser. No. 704,814, filed July 13, 1976, now U.S. Pat. No. 4,068,069, which is a division of Application Ser. No. 430,925, filed Jan. 4, 1974, now U.S. Pat. No. 3,980,643.

The present invention relates to a process of producing a piperazine- or homopiperazine-monoalkanol ester represented by the formula:

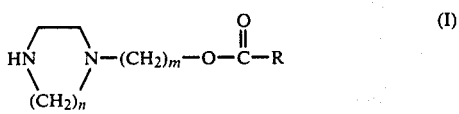

wherein R is a phenyl group which may be substituted with a lower alkyl group, a lower alkoxy group or a halogen atom, or a styryl group or 2-, 3- or a 4- pyridyl group which may be substituted with a lower alkoxy group; and n and m are 2 or 3, respectively, and a salt thereof.

According to the present invention, the compounds represented by the formula (I) above can be produced by esterification of a piperazine- or homopiperazine-monoalkanol represented by the formula:

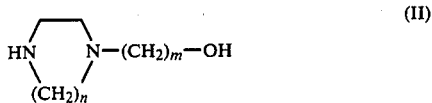

wherein n and m each represents 2 or 3, or a salt thereof, with a benzoic acid which may be substituted with a lower alkyl group, a lower alkoxy group or a halogen atom, or a cinnamic acid or a nicotinic acid compound including nicotinic acid, isonicotinic acid and picolinic acid which may be substituted with a lower alkoxy group.

The esterification in accordance with the present invention proceeds successfully in the presence of a dehydrating agent. Specific examples of suitable dehydrating agents include hydrochloric acid, sulfuric acid, p-toluene sulfonic acid, N,N dicyclohexylcarbodiimide, etc. Among those, p-toluene sulfonic acid is most preferred. Any solvent can be employed in the esterification in accordance with the present invention unless the solvents prevent the reaction. Typical examples of suitable solvents are benzene, toluene, xylene, dioxane, chloroform, tetrahydrofuran, etc., preferably, benzene or dioxane is employed. The preferred reaction temperature is, in general, above room temperature, more preferably, near the boiling point of the solvent employed.

The product (I) produced in accordance with the present invention can be converted into the corresponding salt using an inorganic or organic acid in a conventional manner. Typical examples of inorganic acids include hydrohalic acids hydrochloric acid, hydrobromic acid), sulfuric acid, phosphoric acid, etc. The organic acids which can be employed in the present invention are typified by lactic acid, maleic acid, succinic acid, tartaric acid, salicylic acid, oxalic acid, citric acid, benzoic acid, etc.

The novel compounds (I) in accordance with the present invention exhibits analgetic, coronary vasodilative, anti-convulsant, blood pressure decreasing properties, and such compounds are particularly useful as therapeutic agents in treating circulatory diseases and are further useful as intermediates in preparing for other therapeutic agents.

The following examples are merely illustrative and are not to be considered as limiting the invention.

EXAMPLE 1

In 150 ml of absolute benzene there were dissolved 26 g of 1-piperazineethanol, 5.5 g of 2,3,4-trimethoxybenzoic acid and 19 g of p-toluene sulfonic acid. The solution was heated for 15 hours to reflux while removing the formed water. After the reaction liquid was cooled, the reaction liquid was washed with 15% potassium carbonate and then extracted with 10% hydrochloric acid. After washing the aqueous layer with ether, the system was rendered alkaline with potassium carbonate followed by extraction with ether. The ethereal layer was dehydrated with a Glauber's salt and then the ether was removed by distillation. The resultant residue was subjected to chromatography using silica gel to give a colorless transparent liquid. The liquid was treated in a conventional manner to convert the product into the maleic acid salt thereof. Upon crystallization from ethanol, 1-piperazineethanol 2,3,4-trimethoxybenzoate maleate was obtained exhibiting a melting point of 140°–141° C. The yield was 46%.

Elemental Analysis: as $C_{16}H_{24}N_2O_5.2(C_4H_4O_4).H_2O$.
Calculated: C:50.49 H:5.98 N:5.00.
Found: C:50.37 H:5.97 N:4.88.

EXAMPLE 2

In 150 ml of absolute dioxane there were dissolved 2.88 g of 1-piperazinepropanol, 3.64 g of p-flu orobenzoic acid and 19 g of p-toluene sulfonic acid. While removing the formed water, the solution was heated for 16 hours to reflux. After the dioxane was removed from the reaction liquid, ether was added to the residue. The system was extracted with 10% hydrochloric acid. The aqueous layer was rendered alkaline using potassium carbonate and then extracted with ether. The ethereal layer was dehydrated with a Glauber's salt. The ether was removed from the system by distillation. The resultant residue was subjected to chromatography using silica gel to give a colorless transparent liquid. The liquid was converted into the hydrochloride thereof in accordance with a conventional manner. Upon recrystallization from thanol, 1-piperazinepropanol p-fluorobenzoate hydrochloride was obtained exhibiting a melting point of 196°–199° C. The yield was 56%.

Elemental Analysis: as $C_{14}H_{19}N_2O_2F.2HCl.H_2O$.
Calculated: C:47.07 H:6.49 N:7.84.
Found: C:46.83 H:6.56 N:7.84.

EXAMPLE 3

In 150 ml of absolute benzene there were dissolved 1.44 of 1-homopiperazineethanol and 9.5 g of p-toluene sulfonic acid. To the resulting solution, 2.75 g of 2,3,4-trimethoxybenzoic acid was added. The system was heated for 16 hours to reflux while removing the formed water. The reaction liquid was cooled, washed with 15% potassium carbonate and then extracted with 10% HCl. After the aqueous layer was washed and then rendered alkaline with potassium carbonate, followed by extraction with ether. After the ethereal layer was dehydrated with a Glauber's salt, the ether was distilled off. The resultant residue was subjected to chromatography using silica gel to obtain a colorless transparent liquid. The liquid was converted into the maleic acid salt thereof in accordance with a conventional manner. Upon recrystallization from ethanol, 1-homopiperazineethanol 2,3,4-trimethoxybenzoate maleate was obtained having a melting point of 112°–113° C. The yield was 59%.

Elemental Analysis: as $C_{17}H_{26}N_2O_5.2(C_4H_4O_4).H_2O$.
Calculated: C:51.02 H:6.17 N:4.76.
Found: C:50.91 H:6.25 N:4.71.

EXAMPLE 4

In 150 ml of absolute benzene there were dissolved 288 g of 1-piperazinepropanol, 3.2 g of isonicotinic acid and 30.4 g of p-toluene sulfonic acid. The solution was heated for 15 hours to reflux while removing the formed water. The resulting reaction liquid was cooled, washed with 15% potassium carbonate and then extracted with 10% hydrochloric acid. After the aqueous layer was washed with ether, the system was rendered alkaline with potassium carbonate and then extracted with ether. After the ethereal layer was dehydrated with a Glauber's salt, the ether was distilled off. The resultant residue was subjected to chromatography using silica gel to obtain a colorless transparent liquid. This liquid was converted to the hydrochloride thereof in accordance with a conventional manner. It was recrystallized from ethanol to give 1-piperazinepropanol isonicotinate hydrochloride. The melting point of the product was 201°–202° C. The yield was 66%.

Elemental Analysis: as $C_{13}H_{19}N_3O_2.2HCl.H_2O$.
Calculated: C:45.89 H:6.81 N:12.35.
Found: C:45.75 H:6.92 N:12.31.

EXAMPLE 5

In 150 ml of absolute benzene there were dissolved 3.04 g of 1-homopiperazinepropanol, 2.85 g of picolinic acid and 2.73 g of p-toluene sulfonic acid. The solution was heated for 16 hours to reflux while removing the formed water. The reaction liquid was cooled, washed with 15% potassium carbonate and then extracted with 10% hydrochloric acid. The aqueous layer was washed with ether then rendered alkaline with potassium carbonate followed by extraction with ether. After the ethereal layer was dehydrated over a Glauber's salt, the ether was distilled off. The resultant residue was subjected to chromatography using silica gel to give a colorless transparent liquid. The liquid was converted into the maleic acid salt thereof in accordance with a conventional manner. Upon recrystallization of the maleic acid salt from ethanol, 1-homopiperazinepropanol picolinate maleate was obtained having a melting point of 105°–107° C. The yield was 47%.

Elemental Analysis: as $C_{14}H_{21}N_3O_2.2C_4H_4O_4.H_2O$.
Calculated: C:51.46 H:6.09 N:8.18.
Found: C:51.30 H:6.22 N:8.14.

EXAMPLE 6

In 150 ml of absolute benzene there were dissolved 1.95 g of 1-piperazineethanol and 14.2 g of p-toluene sulfonic acid. To the solution 2.89 g of cinnamic acid was added. The system was heated for 16 hours to reflux while removing the formed water. The reaction liquid was cooled, washed with 15% potassium carbonate and then extracted with 10% hydrochloric acid. After the aqueous layer was washed with ether, the system was rendered alkaline followed by extraction with ether. After the ethereal layer was dehydrated over a Glauber's salt, the ether was distilled off. The resultant residue was subjected to chromatography using silica gel to give a colorless transparent liquid. The liquid was converted into the hydrochloride thereof. Upon recrystallization from ethanol, 1-piperazineethanol cinnamate hydrochloride was obtained. The melting point of the product was 184°–187° C. The yield was 53%.

Elemental Analysis: as $C_{15}H_{20}N_2O_2.2HCl.H_2O$.
Calculated: C:48.66 H:6.53 N:7.56.
Found: C:48.61 H:6.60 N:7.48.

EXAMPLE 7

In 1.50 ml of absolute benzene there were dissolved 1.58 g of 1-homopiperazinepropanol, 3.09 g of 2,3,4-trimethoxycinnamic acid and 9.5 g of p-toluene sulfonic acid. The solution was heated for 16 hours to reflux while removing the formed water. The reaction liquid was cooled, washed with 15% potassium carbonate and then extracted with 10% hydrochloric acid. After the aqueous layer was washed with ether, the system was rendered alkaline with potassium carbonate followed by extraction with ether. After the ethereal layer was dehydrated over a Glauber's salt, the ether was distilled off. The resultant residue was subjected to chromatography using silica gel to obtain a colorless transparent liquid. The liquid was converted into the oxalate thereof in accordance with conventional manner. Upon recrystallization from methanol, 1-homopiperazinepropanol 2,3,4-trimethoxycinnamate oxalate was obtained having a melting point of 156°–158° C. The yield was 48%.

Elemental Analysis: as $C_{20}H_{28}N_2O_5.2C_2H_2O_4.H_2O$.
Calculated: C:50.17 H:5.97 N:4.88.
Found: C:50.03 H:6.18 N:4.75.

The following compounds shown in the table below were obtained in a similar manner using the of Example 1–Example 7.

TABLE

| No. | R | n | m | Salt | Melting Point (°C.) |
|---|---|---|---|---|---|
| 1. | 2,3,4-trimethoxyphenyl (OCH₃, OCH₃, OCH₃) | 2 | 2 | Maleate | 150–151.5 |
| 2. | " | 3 | 2 | " | 139–141 |
| 3. | " | 2 | 3 | " | 156.5–158.5 |
| 4. | " | 3 | 3 | " | 146–148 |

TABLE-continued

| No. | R | n | m | Salt | Melting Point (°C.) |
|---|---|---|---|---|---|
| 5. | (2,3,4-trimethoxyphenyl: OCH₃, OCH₃, OCH₃) | 2 | 3 | " | 141-143 |
| 6. | " | 3 | 3 | " | 144.5-145.5 |
| 7. | (2,3-dimethoxyphenyl: OCH₃, OCH₃) | 2 | 3 | Hydrochloride | 204-206 |
| 8. | " | 3 | 3 | Maleate | 154-156 |
| 9. | (3-methylphenyl: CH₃) | 2 | 3 | Hydrochloride | 180-183 |
| 10. | " | 3 | 3 | Maleate | 146-148 |
| 11. | (2-chlorophenyl: Cl) | 2 | 3 | " | 122-123.5 |
| 13. | (4-fluorophenyl: F) | 3 | 3 | Hydrochloride | 175-177 |
| 14. | (phenyl) | 2 | 3 | " | 178.5-181 |
| 15. | " | 3 | 3 | Maleate | 133-134 |
| 16. | (2-pyridyl) | 2 | 2 | " | 127-128 |
| 17. | " | 2 | 3 | " | 138-140 |
| 18. | (3-pyridyl) | 2 | 2 | " | 137-138 |
| 19. | " | 2 | 3 | " | 158-159 |
| 20. | " | 3 | 2 | " | 119-121 |
| 21. | " | 3 | 3 | " | 148-149 |
| 22. | (4-pyridyl) | 2 | 2 | " | 146-147 |
| 23. | " | 3 | 2 | " | 112-115 |
| 24. | " | 3 | 3 | " | 127-130 |
| 25. | —CH=CH—(phenyl) | 2 | 3 | Hydrochloride | 198-200 |
| 26. | " | 3 | 2 | Maleate | 138-141 |
| 27. | " | 3 | 3 | " | 139-140 |
| 28. | —CH=CH—(3,4,5-trimethoxyphenyl: OCH₃, OCH₃, OCH₃) | 2 | 2 | " | 127-128 |
| 29. | " | 2 | 3 | " | 134-135 |
| 30. | " | 3 | 2 | Oxalate | 150-151 |
| 31. | " | 3 | 3 | Maleate | 108-110 |

TABLE-continued

| No. | R | n | m | Salt | Melting Point (°C.) |
|-----|---|---|---|------|---------------------|
| 32. | 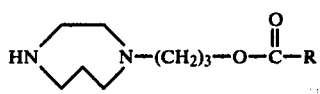 | 2 | 2 | " | 123–124.5 |
| 33. | " | 2 | 3 | " | 134–135.5 |
| 34. | " | 3 | 2 | Oxalate | 158–161 |

While the invention has been described in detail and with reference to specific embodiments thereof, it will be apparent to one skilled in the art that various changes and modifications can be made therein without departing from the spirit and scope thereof.

What is claimed is:

1. A method of providing coronary vasodilative or blood pressure decreasing effect which comprises administering an effective amount of a compound of the formula $$HN\diagup\diagdown N-(CH_2)_3-O-\overset{O}{\underset{\|}{C}}-R$$

wherein R represents phenyl tri-substituted by lower alkoxy, or a pharmaceutically acceptable salt thereof.

2. A method according to claim 1 wherein the compound administered is of the formula

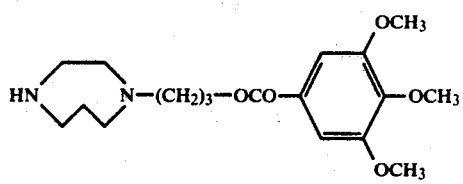

3. A method according to claim 1 wherein the compound administered is of the formula

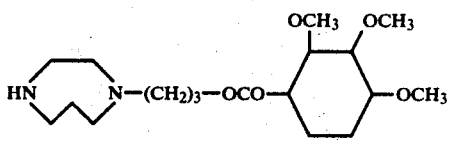

or the hydrochloride salt thereof.

* * * * *

UNITED STATES PATENT AND TRADEMARK OFFICE
CERTIFICATE OF CORRECTION

PATENT NO. : 4,169,144  Page 1 of 2
DATED : September 25 1979
INVENTOR(S) : Hideo Kato, et al It is certified that error appears in the above—identified patent and that said Letters Patent is hereby corrected as shown below:

The title, on title page and at top of column 1 is incorrect and should read: --TRIALKOXYPHENYLESTERS OF HOMOPIPERAZINE-N-MONOALKANOL USEFUL AS VASODILATORS--.

Column 1, line 22:  Before "2-," insert --a--.

line 63:  Before "hydrochloric" insert --(--.

Column 2, line 6:  Delete "for".

line 51:  "thanol" should be --ethanol--.

line 60:  After "1.44" insert --g--.

Column 3, line 17:  After "The" insert --resulting--.

line 19:  After "The" delete "resulting".

line 45:  After "ether" insert a comma.

Column 6, in the Table under "Melting Point (°C.)" for "No. 11": "122-123.5" should be --149-150--.

UNITED STATES PATENT AND TRADEMARK OFFICE
CERTIFICATE OF CORRECTION

PATENT NO. : 4,169,144

DATED : September 25, 1979

INVENTOR(S) : Hideo Kato, et al

It is certified that error appears in the above—identified patent and that said Letters Patent is hereby corrected as shown below:

Columns 5 and 6 in the Table: Item No. 12 is missing and should be set out as follows:

| No. | R | n | m | Salt | Melting Point (°C.) |
|-----|---|---|---|------|---------------------|
| 12. | " | 3 | 3 | " | 122-123.5 |

Signed and Sealed this

Seventeenth Day of June 1980

[SEAL]

Attest:

SIDNEY A. DIAMOND

Attesting Officer     Commissioner of Patents and Trademarks